(12) United States Patent
Lin et al.

(10) Patent No.: US 10,570,365 B2
(45) Date of Patent: Feb. 25, 2020

(54) AUTOMATIC CELL ISOLATION AND COLLECTION SYSTEM

(71) Applicant: Kaohsiung Medical University, Kaohsiung (TW)

(72) Inventors: Che-Hsin Lin, Kaohsiung (TW); Yao-Hsien Wang, Kaohsiung (TW); Chung-Hwan Chen, Kaohsiung (TW); Je-Ken Chang, Kaohsiung (TW); Mei-Ling Ho, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 266 days.

(21) Appl. No.: 15/850,320

(22) Filed: Dec. 21, 2017

(65) Prior Publication Data
US 2018/0328824 A1   Nov. 15, 2018

(30) Foreign Application Priority Data

May 15, 2017   (TW) .............................. 106115926 A (51) Int. Cl.
| | |
|---|---|
| *C12M 1/00* | (2006.01) |
| *G01N 1/28* | (2006.01) |
| *B04B 13/00* | (2006.01) |
| *B04B 5/10* | (2006.01) |
| *G01N 35/00* | (2006.01) |

(Continued)

(52) U.S. Cl.
CPC ............. *C12M 47/04* (2013.01); *B01L 3/021* (2013.01); *B01L 9/54* (2013.01); *B04B 5/10* (2013.01); *B04B 13/00* (2013.01); *C12M 45/00* (2013.01); *C12M 45/02* (2013.01); *C12M 45/05* (2013.01); *G01N 1/286* (2013.01); *G01N 1/4077* (2013.01); *G01N 35/0098* (2013.01); *G01N 35/1083* (2013.01); *B01L 2200/0652* (2013.01); *B01L 2400/043* (2013.01); *B04B 2005/105* (2013.01); *B04B 2011/046* (2013.01); *G01N 2001/2866* (2013.01); *G01N 2001/4083* (2013.01); *G01N 2035/00495* (2013.01);

(Continued)

(58) Field of Classification Search
USPC ....... 422/533, 547, 548, 560, 561, 186, 268, 422/292, 304; 436/174, 177
See application file for complete search history.

(56) References Cited

U.S. PATENT DOCUMENTS

| | | | | |
|---|---|---|---|---|
| 5,254,076 | A  * | 10/1993 | Chow ................ | B01D 11/0476 |
| | | | | 494/37 |
| 7,867,444 | B2 * | 1/2011  | Testrut .................... | B01L 9/06 |
| | | | | 211/132.1 |

(Continued)

*Primary Examiner* — Dean Kwak
(74) *Attorney, Agent, or Firm* — MLO, a professional corp.

(57) ABSTRACT

An automatic cell isolation and collection system for sorting out target cells from a sample includes a crush module, a centrifuge module, a transport module, and a control unit. The centrifuge module includes centrifuge tubes and a magnetic mechanism providing a magnetically attractive force to at least one of the centrifuge tubes. The control unit electrically communicates with the crush module, the centrifuge module, and the transport module, and controls operation of the crush module, transport of the sample via the transport module after the sample is crushed by the crush module, centrifugation of the centrifuge module, and operation of the magnetic mechanism for providing the magnetically attractive force.

11 Claims, 13 Drawing Sheets

(51) Int. Cl.
*G01N 35/10* (2006.01)
*C12M 1/33* (2006.01)
*B01L 3/02* (2006.01)
*B01L 9/00* (2006.01)
*G01N 1/40* (2006.01)
*B04B 11/04* (2006.01)

(52) U.S. Cl.
CPC ........... *G01N 2035/00574* (2013.01); *G01N 2035/103* (2013.01); *G01N 2035/106* (2013.01)

(56) References Cited

U.S. PATENT DOCUMENTS

| | | | | |
|---|---|---|---|---|
| 8,317,672 | B2* | 11/2012 | Nash | A61M 1/3693 |
| | | | | 494/10 |
| 2003/0032171 | A1* | 2/2003 | Gemmell | G01N 35/0092 |
| | | | | 435/286.2 |
| 2015/0118752 | A1* | 4/2015 | Cimino | C12M 45/02 |
| | | | | 435/379 |

* cited by examiner

AUTOMATIC CELL ISOLATION AND COLLECTION SYSTEM

CROSS-REFERENCE TO RELATED APPLICATION

This application claims priority of Taiwanese Patent Application No. 106115926, filed on May 15, 2017.

FIELD

The disclosure relates to an isolation and collection system, and more particularly to an automatic cell isolation and collection system.

BACKGROUND

Figure 1:
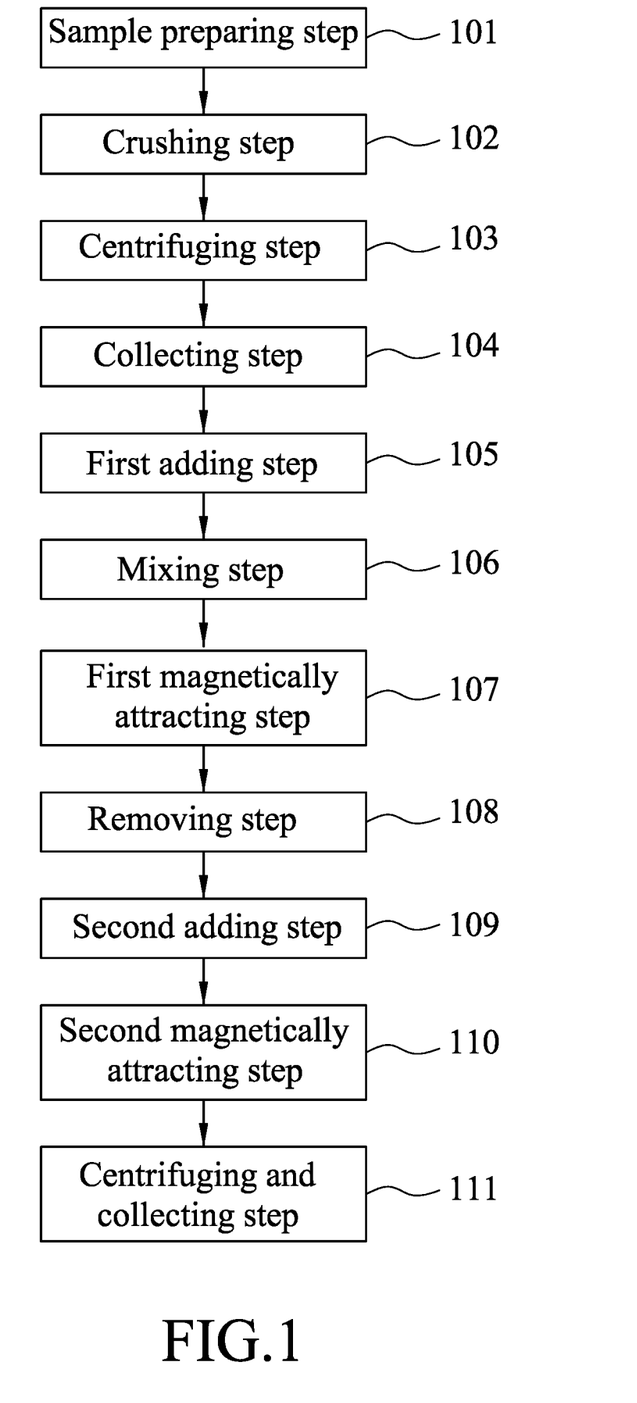
FIG. 1 is a flowchart illustrating a conventional method for cell isolation and collection.

For research purpose or medical procedure, oftentimes it is required to separate a specific type of cells from a tissue taken from a living body for further analysis or for performing a biopsy. Referring to FIG. 1, a conventional cell isolation and collection method includes the follow steps: a sample preparing step 101 in which a tissue sample is prepared, a crushing step 102 in which the tissue sample is crushed, a centrifuging step 103 in which the crushed tissue sample is aliquoted into a number of centrifuge tubes and is centrifuged, a collecting step 104 in which pellet in each of the centrifuge tubes is collected, a first adding step 105 in which the pellet of each centrifuge tube is transferred into another centrifuge tube and a solution containing antibody-conjugated magnetic beads is added thereinto, a mixing step 106 in which the pellets and the solution are fully mixed so as to conjugate the target cells with the beads, a first magnetically attracting step 107 in which a magnetically attractive force is provided to move the beads conjugated with the target cells to bottom parts of the centrifuge tubes, a removing step 108 in which the supernatant is removed from each of the centrifuge tubes, a second adding step 109 in which an enzyme solution is added to break the conjugation between the beads and the target cells, a second magnetically attracting step 110 in which the magnetically attractive force is provided to magnetically attract the beads and the target cells are then moved into different centrifuge tubes, and a centrifuging and collecting step 111 in which a cycle of centrifuging the target cells, removing supernatants, and adding buffer for mixing is repeated for a number of times.

The above-mentioned cell isolation and collection method is relatively complicated, and at least part of the operation in each of the steps is performed by a human operator, which is attention demanding. In addition, the purity of the target cells may be adversely affected by human operator error, and the efficiency of the entire operation is relatively low.

SUMMARY

Therefore, an object of the disclosure is to provide an automatic cell isolation and collection system that can alleviate at least one of the drawbacks of the prior art.

According to the disclosure, the automatic cell isolation and collection system is adapted for sorting out target cells from a sample. The automatic cell isolation and collection system includes a crush module, a centrifuge module, a transport module, and a control unit.

The crush module includes a container that defines an accommodating space adapted for receiving the sample therein, and a crusher that is removably disposed in the accommodating space and that is for crushing the sample.

The centrifuge module is spaced apart from the crush module, and includes a centrifuge seat, a plurality of spaced-apart centrifuge tubes that are disposed on the centrifuge seat, and a magnetic mechanism that is spaced apart from the centrifuge seat, and that provides a magnetically attractive force to at least one of the centrifuge tubes.

The transport module is disposed along a path between the crush module and the centrifuge module, and includes a movable connecting seat, and a pipettor that is co-movably connected to the connecting seat and that is for transferring of the sample and for transferring of a reagent to the centrifuge tubes.

The control unit is in electrical communication with the crush module, the centrifuge module, and the transport module, and controls crushing operation of the crush module, transport of the sample via the transport module after the sample is crushed by the crush module, centrifugation of the centrifuge module, and operation of the magnetic mechanism for providing the magnetically attractive force.

BRIEF DESCRIPTION OF THE DRAWINGS

Other features and advantages of the disclosure will become apparent in the following detailed description of the embodiment with reference to the accompanying drawings, of which.

DETAILED DESCRIPTION

Figure 2:
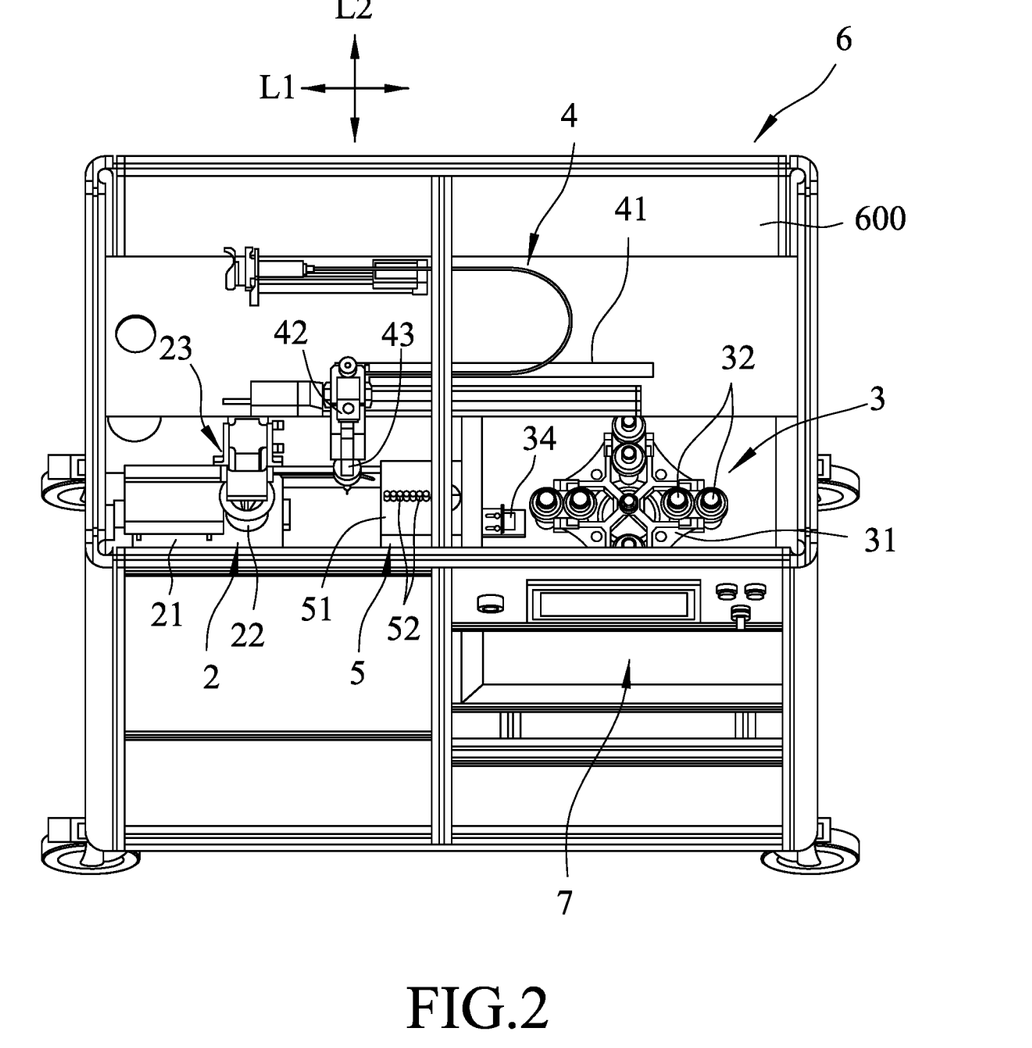
FIG. 2 is a perspective view illustrating an embodiment of an automatic cell isolation and collection system according to the disclosure.
Figure 3:
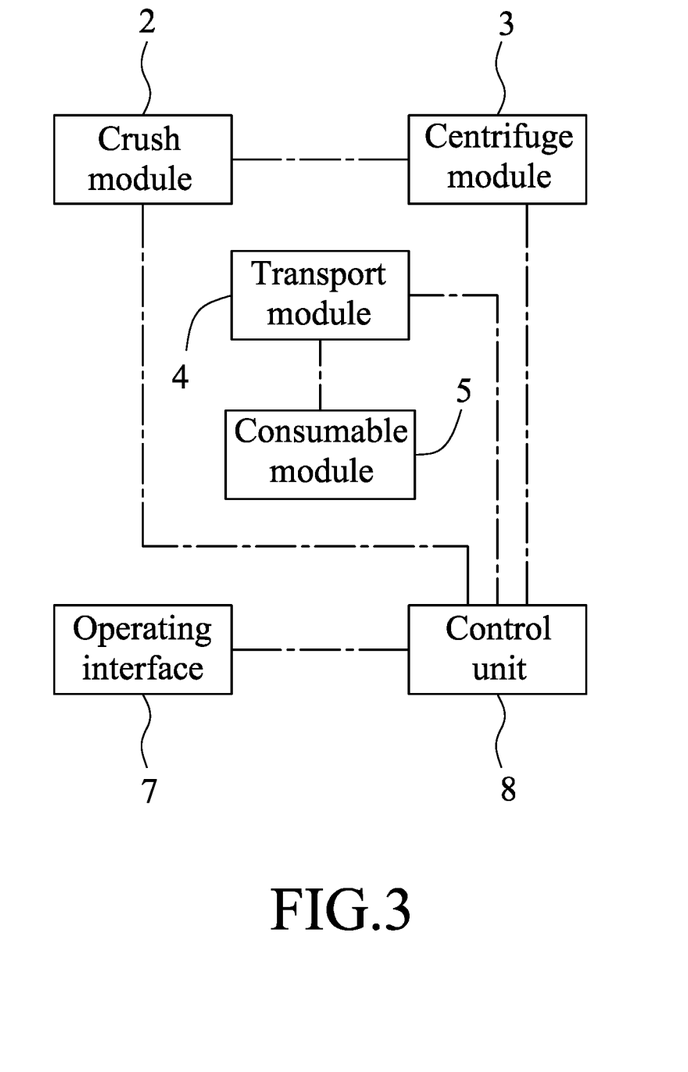
FIG. 3 is a schematic diagram illustrating relationship between components of the embodiment.
Figure 4:
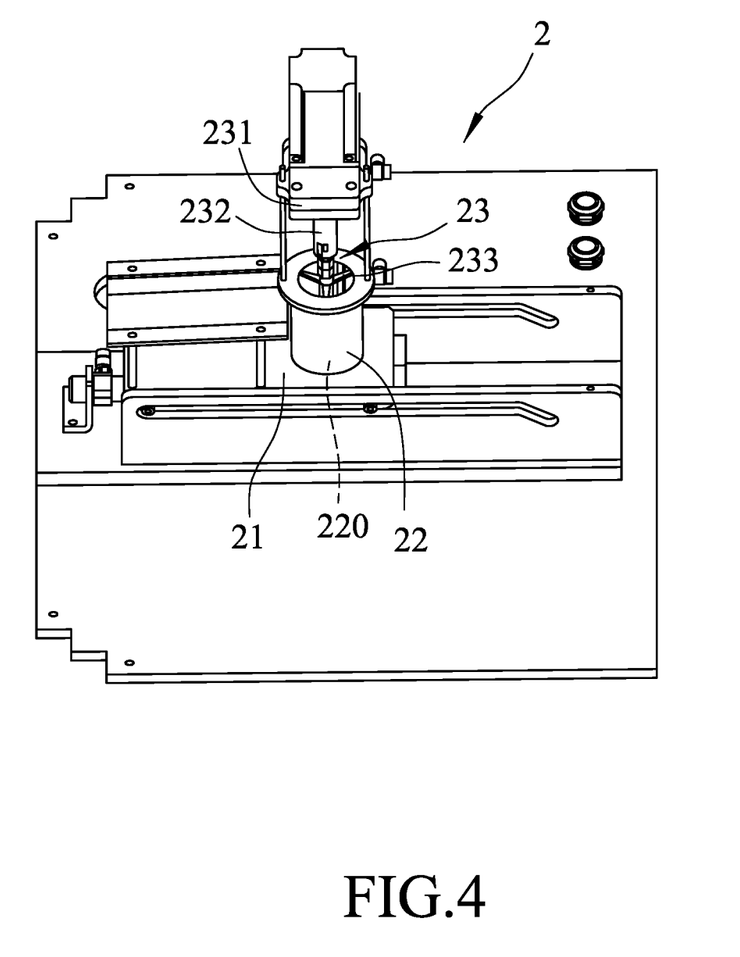
FIG. 4 is an enlarged perspective view illustrating a crush module of the embodiment.

Referring to FIGS. 2 to 4, an embodiment of an automatic cell isolation and collection system according to the disclosure is adapted for sorting out target cells 92 (see FIGS. 12 and 13) from a sample. It should be noted that the sample exemplified in this embodiment is a tissue sample directly taken from a living body, and the target cells 92 exemplified in this embodiment are stem cells. However, the application of the automatic cell isolation and collection system of the disclosure is not limited thereto.

The automatic cell isolation and collection system includes a crush module 2, a centrifuge module 3, a transport module 4, a consumable module 5, a housing 6, an operating interface 7, and a control unit 8. The crush module 2 and the centrifuge module 3 are spaced apart from each other in a first direction (L1).

The crush module 2 includes a movable platform 21 that is operable to move in the first direction (L1), a container 22 that is disposed on the movable platform 21 and that defines an accommodating space 220 adapted for receiving the sample therein, and a crusher 23 that is removably disposed in the accommodating space 220 and that is for crushing the sample. The crusher 23 includes a rotor 231, a drive shaft 232 driven rotatably by the rotor 231, and a blade 233 disposed on the drive shaft 232 and configured to crush the sample when the drive shaft 232 is rotated.

Figure 5:
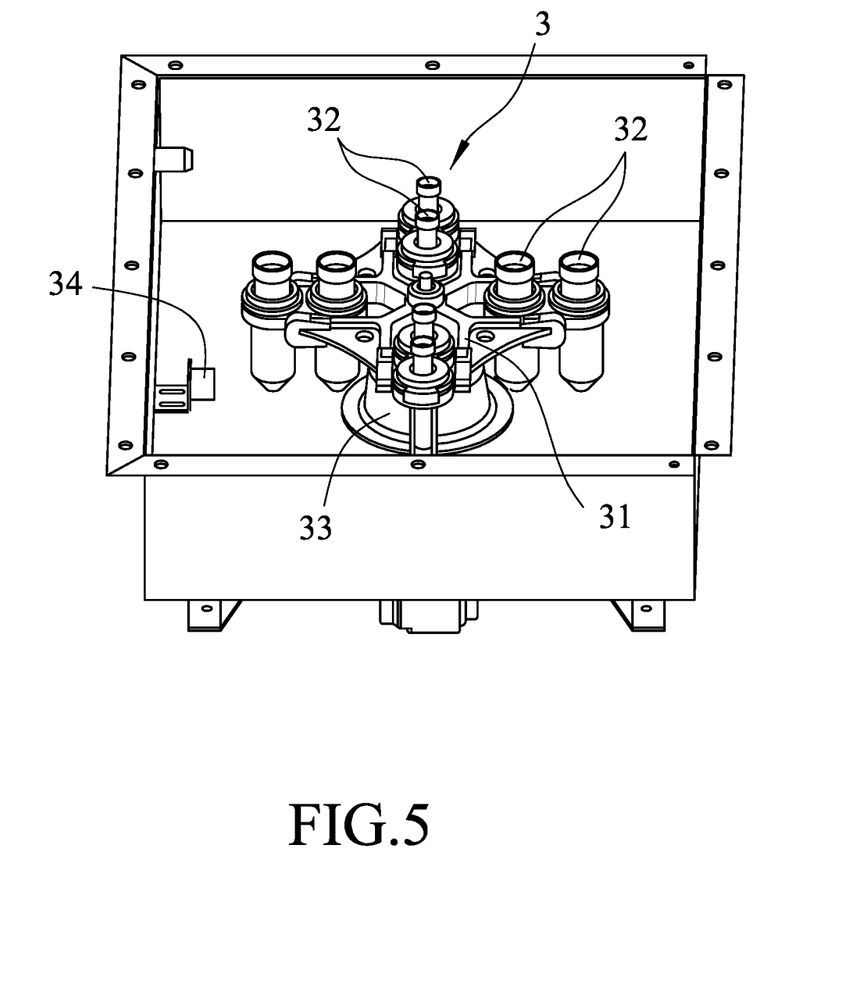
FIG. 5 is an enlarged perspective view illustrating a centrifuge module of the embodiment.

Referring to FIGS. 2, 3, and 5, the centrifuge module 3 includes a centrifuge seat 31, a plurality of spaced-apart centrifuge tubes 32 that are symmetrically disposed on the centrifuge seat 31, a step motor 33 that is connected to the centrifuge seat 31 and that is in electrical communication with the control unit 8, and a magnetic mechanism 34 that is spaced apart from the centrifuge seat 31 and that provides a magnetically attractive force to at least one of the centrifuge tubes 32. In this embodiment, the magnetic mechanism 34 is a permanent magnet, and is operable by the control unit 8 to move between a magnetically attracted position, where the magnetic mechanism 34 is proximate to the at least one of the centrifuge tubes 32 so as to provide the magnetically attractive force to the at least one of the centrifuge tubes 32, and a magnetically non-attracted position, where the magnetic mechanism 34 is distal from the at least one of the centrifuge tubes 32. In other modification of this embodiment, the magnetic mechanism 34 may be an electromagnet that is operable by the control unit 8 to generate the magnetically attractive force.

Figure 6:
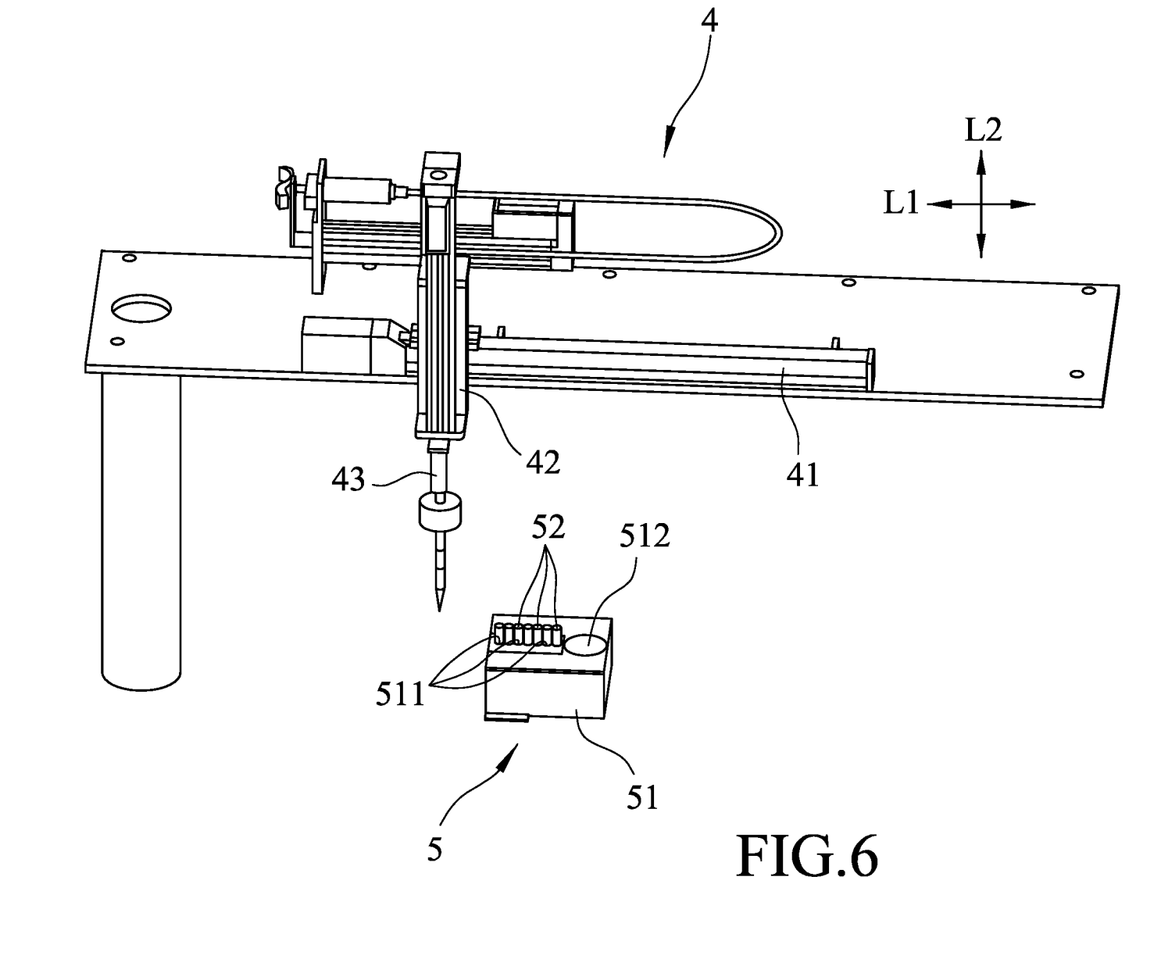
FIG. 6 is an enlarged perspective view illustrating a transport module and a consumable module of the embodiment.

Referring to FIGS. 2 and 6, the transport module 4 is disposed along a path in the first direction (L1) between the crush module 2 and the centrifuge module 3. The transport module 4 includes a linear rail 41 that extends in the first direction (L1) and that is located above the crush module 2 and the centrifuge module 3, a movable connecting seat 42 that is disposed on and slidable along the linear rail 41, and a pipettor 43 that is co-movably connected to the connecting seat 42 and that is for transferring of the sample and for transferring of a reagent to the centrifuge tubes 32. More specifically, the pipettor 43 is co-movable with the connecting seat 42 in the first direction (L1), and the pipettor 43 is movable reciprocately relative to the linear rail 41 in a second direction (L2) which is transverse to the first direction (L1).

The consumable module 5 is disposed between the crush module 2 and the centrifuge module 3, is located under the transport module 4, and includes a tip case 51 and a plurality of pipette tips 52. The tip case 51 is formed with a plurality of tip-receiving holes 511 facing upward, and a disposal space 512 spaced apart from tip-receiving holes 511. Each of the pipette tips 52 is disposed in a corresponding one of the tip-receiving holes 511, and fits on the pipettor 43. In order to prevent cross contamination of the sample and reagents used during the isolation and collection process which may undesirably affect yield of the process, each of the pipette tips 52 is disposed in the disposal space 512 for disposal once it is used.

The housing 6 defines a closed space 600 in which the crush module 2, the transport module 4, the centrifuge module 3, and the consumable module 5 are disposed, so as to eliminate the introduction of microorganisms and other contaminants during a cell isolation and collection process. In actual practice, the housing 6 may be configured to be aseptic. It is worth mentioning that only a frame part of the housing 6 is shown in the figures for the sake of clarity. The automatic cell isolation and collection system is a closed system in this embodiment.

The operating interface 7 is disposed on the housing 6 and electrically communicates with the control unit 8.

The control unit 8 is in electrical communication with the crush module 2, the centrifuge module 3, and the transport module 4. The control unit 8 controls crushing operation of the crush module 2, transport of the sample via the transport module 4 after the sample is crushed by the crush module 2, centrifugation of the centrifuge module 3, and operation of the magnetic mechanism 34 for providing the magnetically attractive force.

Figure 7:
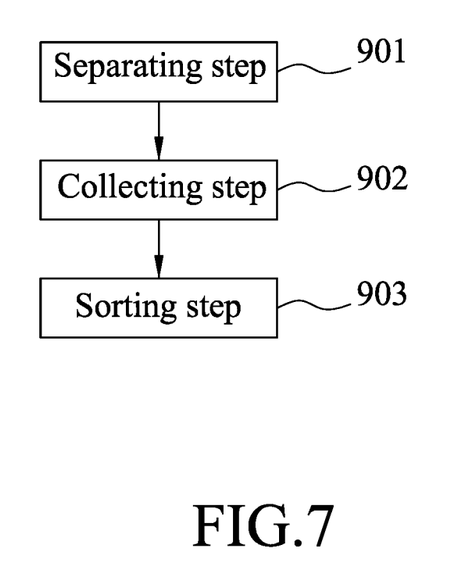
FIG. 7 is a flowchart illustrating steps of a cell isolation and collection process using the embodiment.

Referring to FIG. 7, a cell isolation and collection process using the embodiment is described in detail in the following. The process includes a separating step 901, a collecting step 902, and a sorting step 903.

Figure 8:
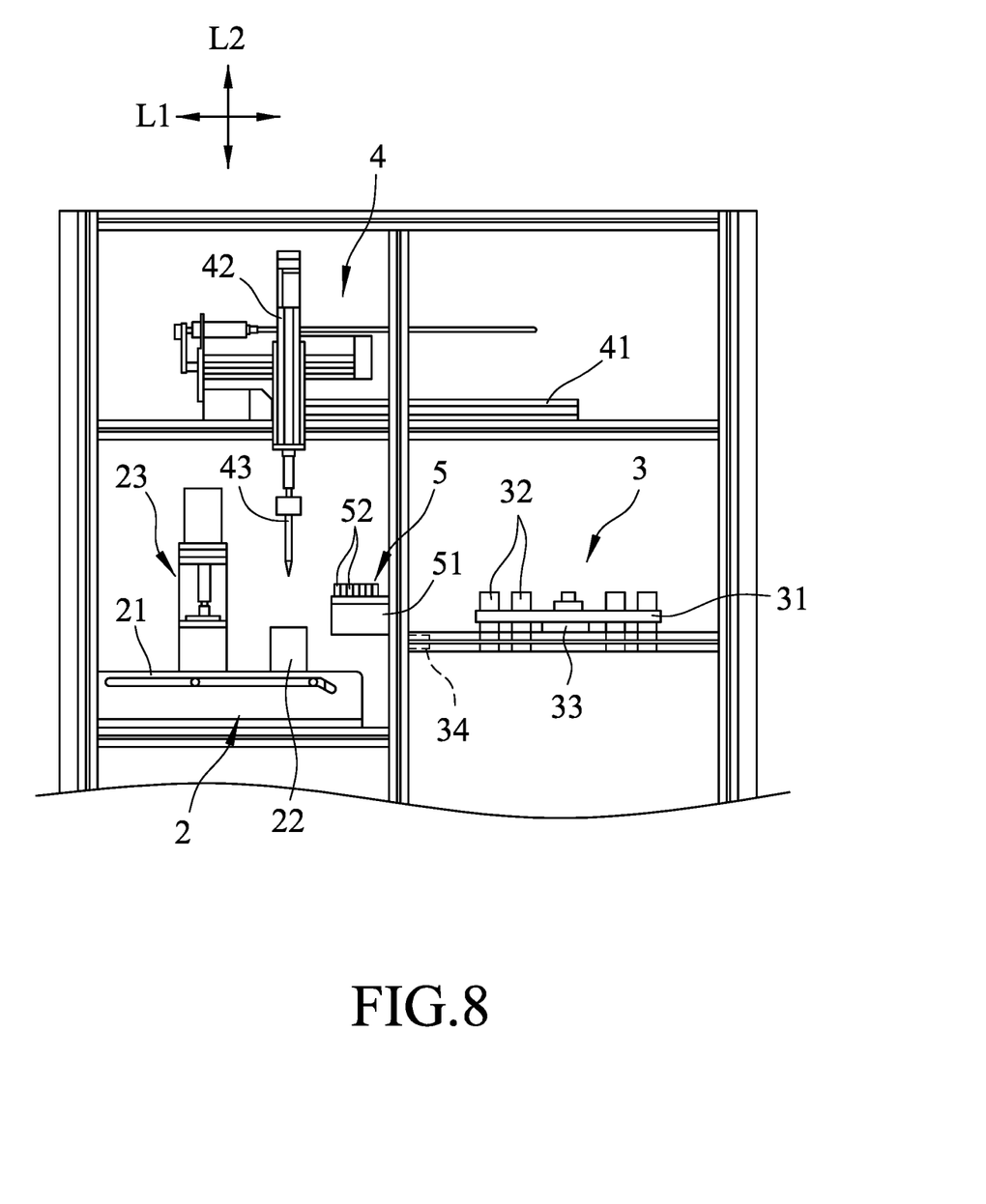
FIGS. 8 to 10 are fragmentary schematic views illustrating operation of the embodiment.

Referring to FIGS. 4, 7, and 8, in the separating step 901, first the sample is placed in the accommodating space 220 of the container 22, and the rotor 231 is actuated by the control unit 8 to drive rotation of the drive shaft 232 and the blade 233 to crush the sample. Subsequently, the pipettor 43 is moved along the linear rail 41 to a position directly above the consumable module 5 (see FIG. 9), and then is moved downward so that one of the pipette tips 52 is fitted on the pipettor 43. Next, a buffer solution is added into the accommodating space 220 using the pipettor 43. Upon addition of the buffer solution, part of the crushed tissue sample attached to the blade 233 can be washed down for removal from the blade 233, and a sample solution containing the crushed tissue sample and the buffer solution is obtained. At this time, the pipette tip 52 on the pipettor 43, which is used to transfer the buffer solution into the accommodating space 220, is disposed in the disposal space 512 of the tip case 51, and another one of the pipette tips 52 is fitted onto the pipettor to transfer the sample solution to one of the centrifuge tubes 32 of the centrifuge module 3.

It is worth mentioning that in this embodiment, the buffer solution is normal saline, but is not limited thereto as long as the buffer solution can provide stability to the crushed sample and does not adversely affect the physical and chemical properties of the sample. In addition, a new pipette tip 52 of the consumable module 5 is used each time when adding a reagent or transferring the sample using the pipettor 43 so as to prevent cross contamination that may lead to unexpected result. In the following, the steps of disposing a used pipette tip 52 to the disposal space 512 and fitting the pipettor 43 with a new pipette tip 52 from the tip case 51 are not described in detail for the sake of clarity.

Figure 10:
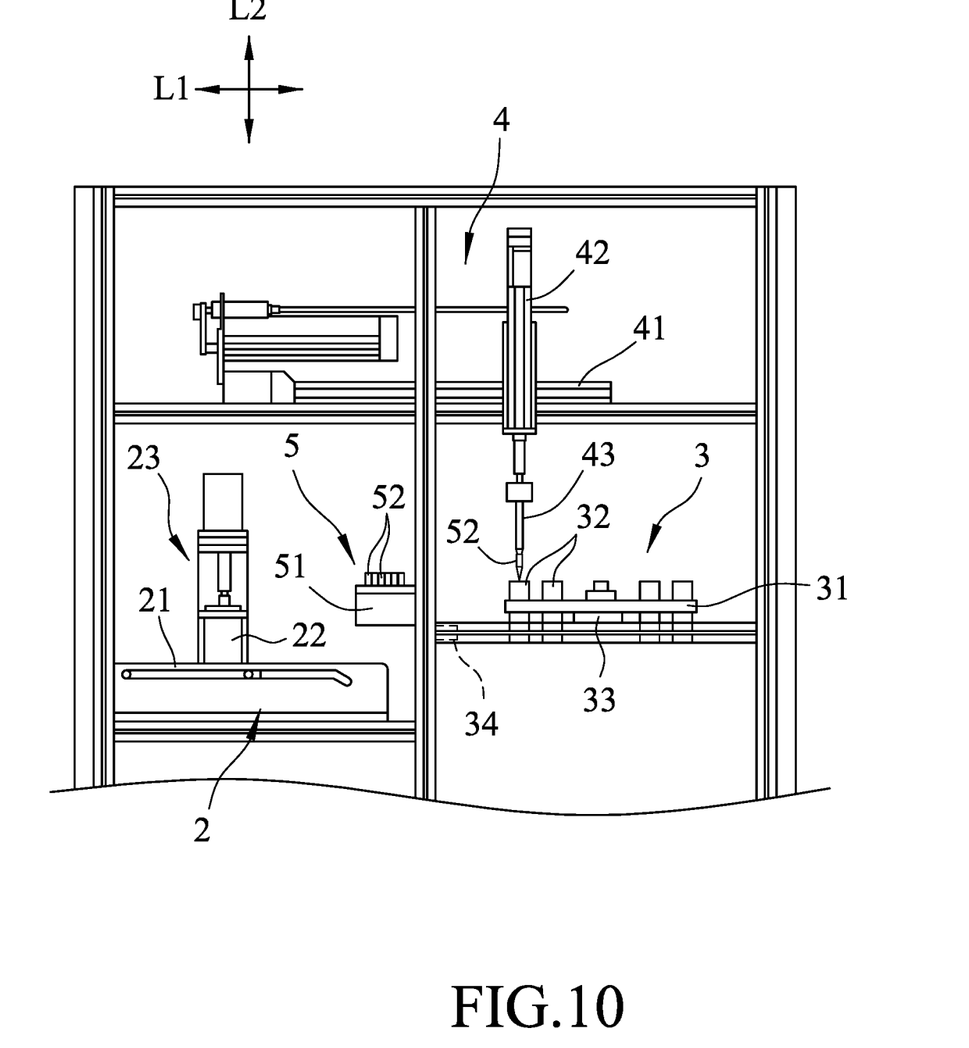

Referring to FIGS. 3, 7, and 10, in the collecting step 902, the centrifuge seat 31 is operated to rotate (i.e., centrifuging) to separate lipid in the sample solution. Since lipid has a lower density than the target cells 92, the target cells 92 form a pellet at a bottom of each of the centrifuge tubes 32 after centrifuging. The pellet in each centrifuge tube 32 is transferred to another centrifuge tube 32 by using the pipettor 43.

Figure 11:
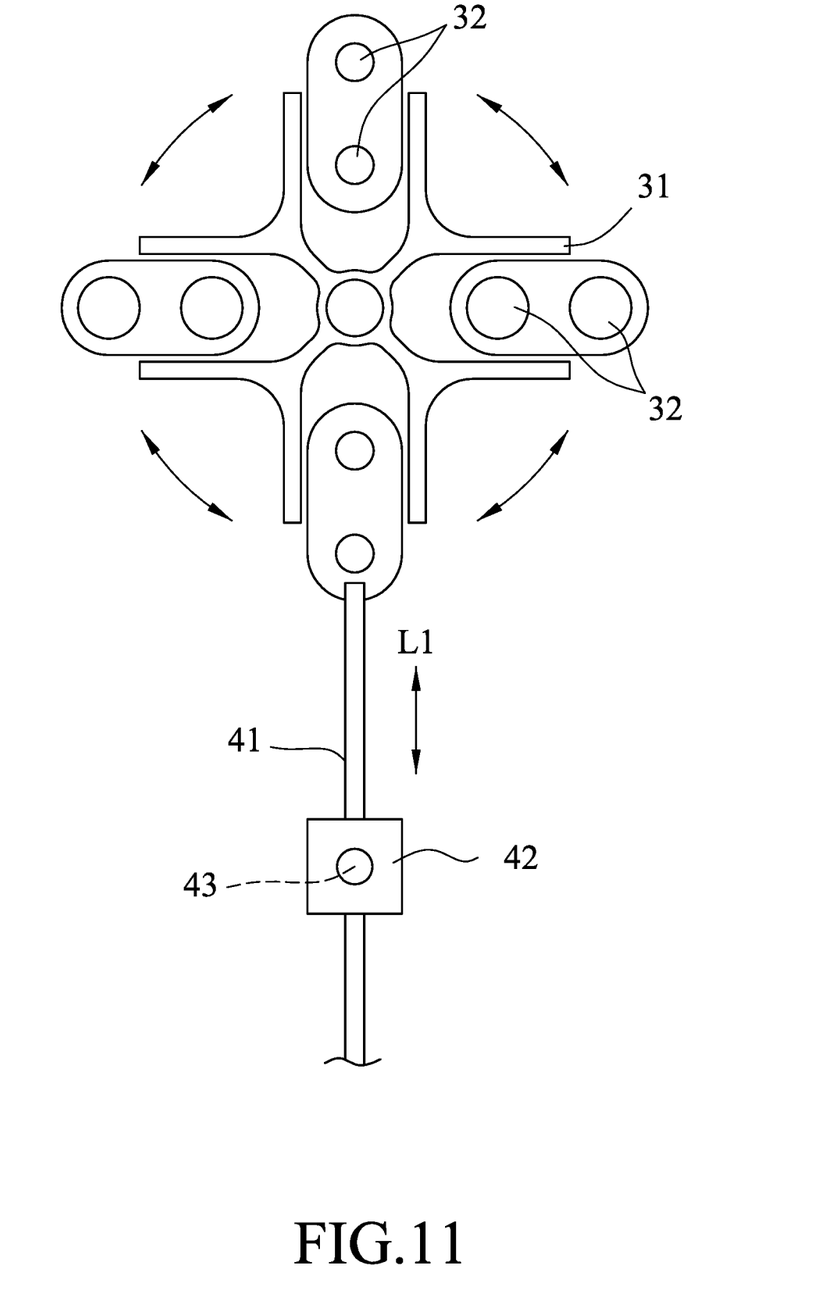
FIG. 11 is a fragmentary schematic top view illustrating operations of the transport module and the centrifuge module of the embodiment.

It should be noted that since the pipettor 43 can only be moved in the first direction (L1), whenever content in any one of the centrifuge tubes 32 is to be transferred using the pipettor 43, the control unit 8 controls the rotation of the step motor 33 so that the centrifuge tubes 32 are moved to positions that can be operated by the pipettor 43, as illustrated in FIG. 11.

Figure 9:
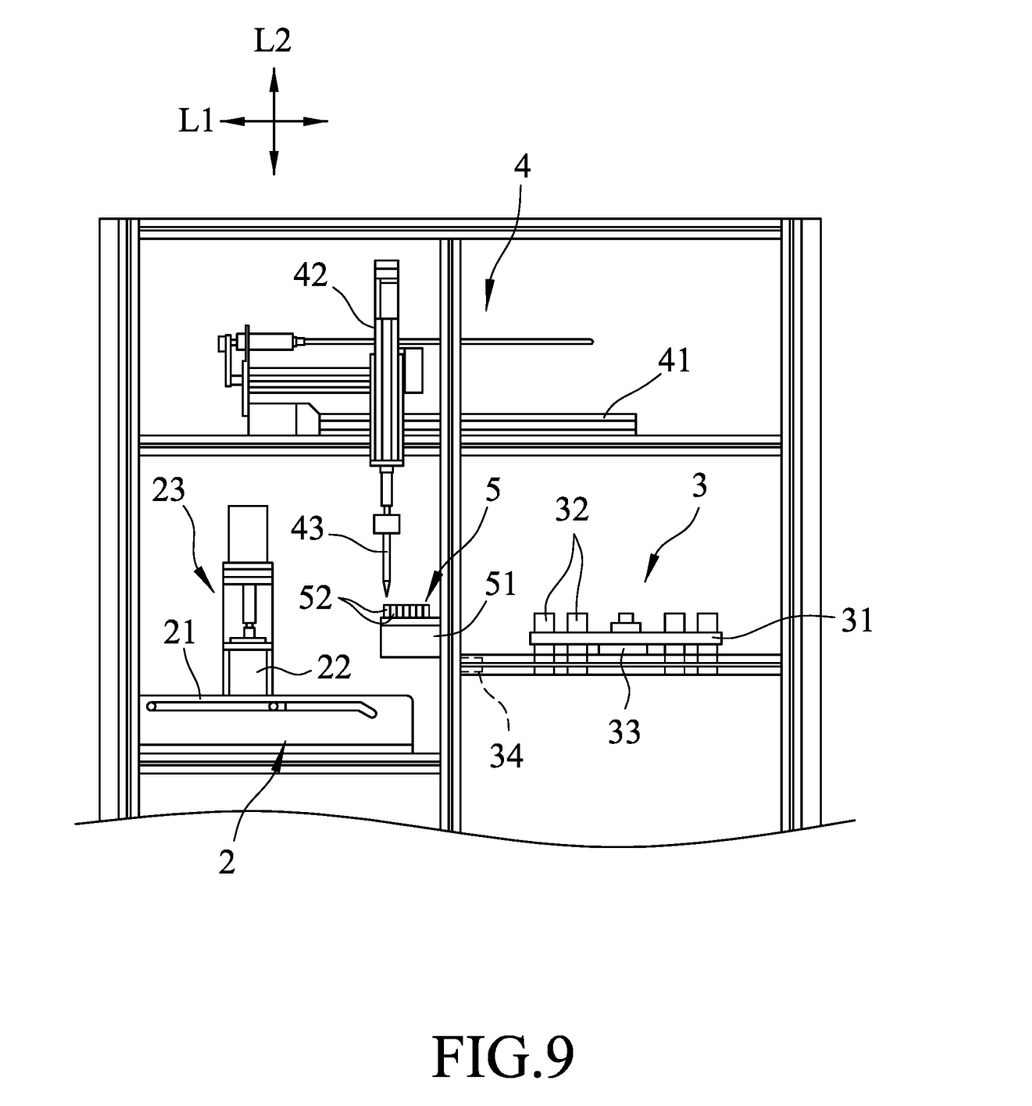

Referring to FIGS. 9 and 10, a hypotonic solution is added to the centrifuge tubes 32 containing the target cells 92 and then is mixed by pipetting action so that red blood cells in the sample are ruptured due to osmotic pressure. Afterwards, centrifugation is performed and the pellet containing the target cells 92 in each centrifuge tube 32 is transferred to another centrifuge tube 32 by using the pipettor 43 under the operation of the step motor 33.

At this time, each centrifuge tube 32 still contains cells other than the target cells 92. In order to isolate the target cells 92, a sorting step 903 is performed. First, a solution containing antibody-conjugated magnetic beads 91 is added into the centrifuge tubes 32 containing the target cells 92 by using the pipettor 43, and repeated pipetting action is performed for uniformly mixing the beads 91 and the target cells 92 so that the beads 91 can be conjugated to the target cells 92. Since the features of this disclosure does not reside in the conjugation of the magnetic beads 91 and the target cells 92, further details of the same are not provided herein for the sake of brevity.

Figure 12:
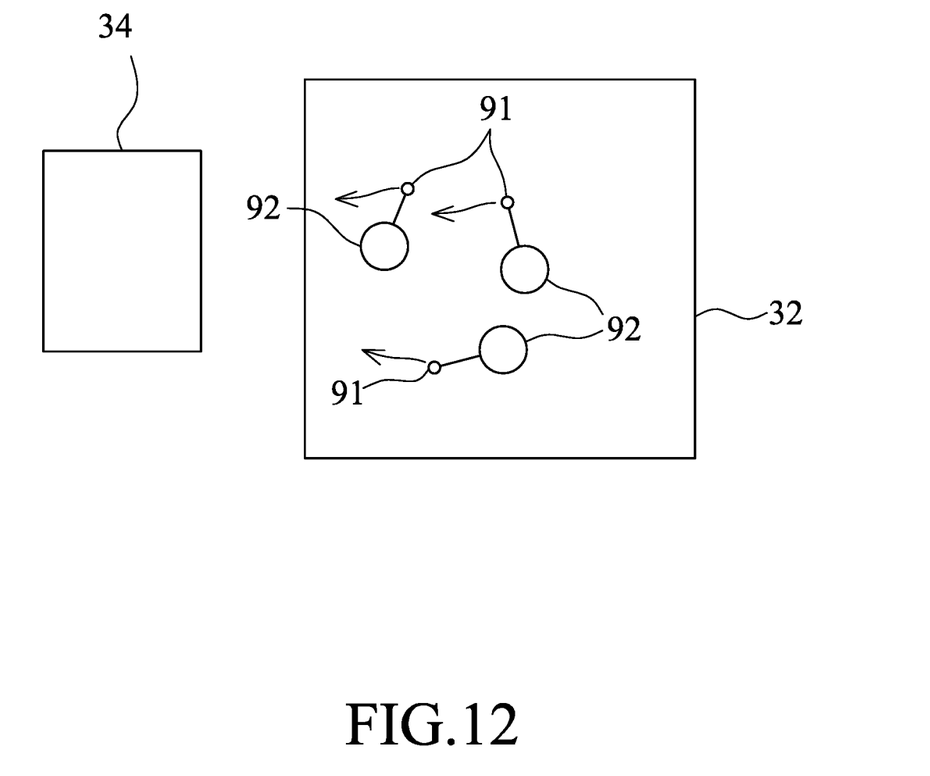
FIGS. 12 and 13 are schematic views illustrating operation of a magnetic mechanism of the centrifuge module of the embodiment.
Figure 13:
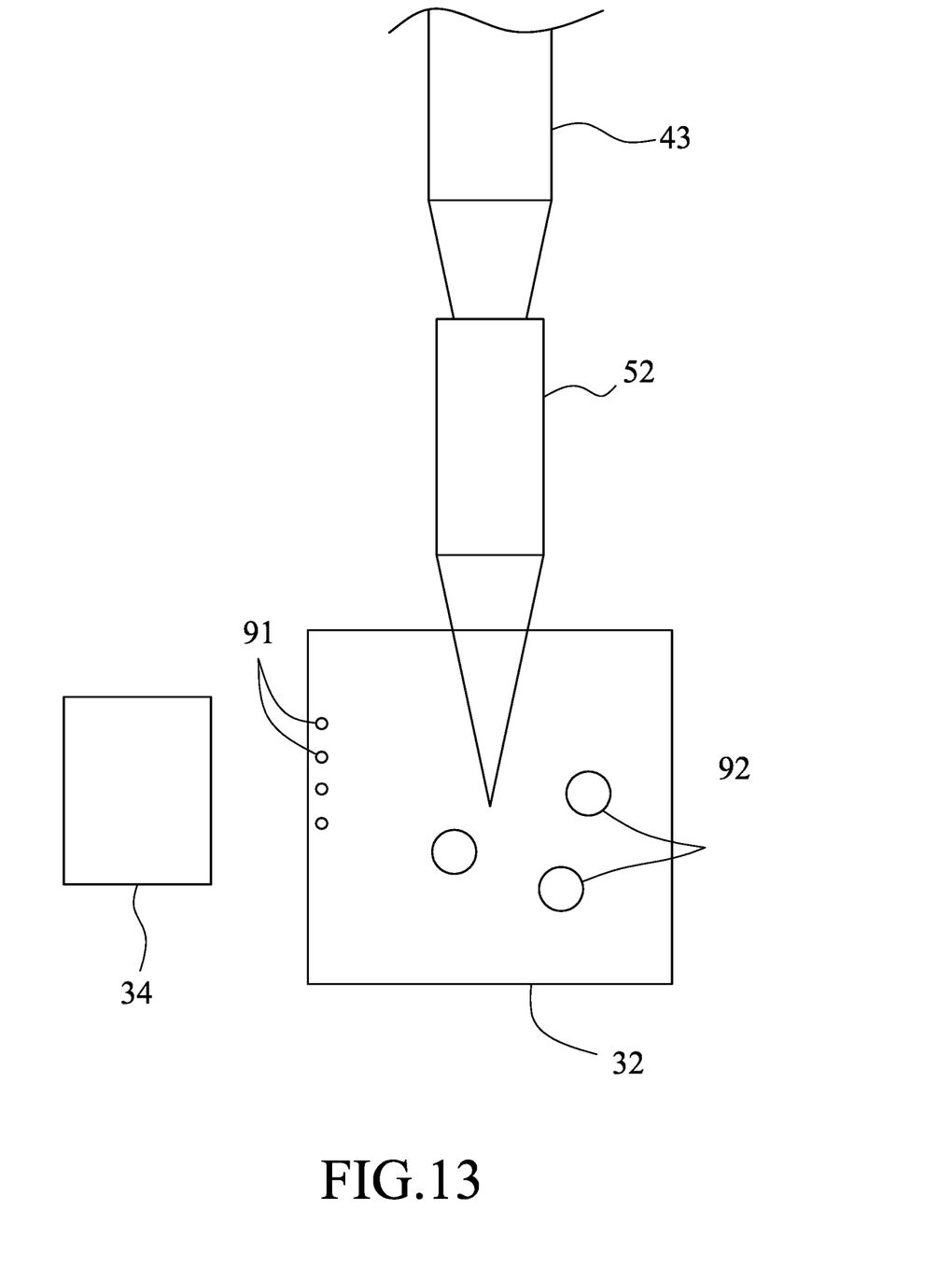

Subsequently, the control unit 8 controls movement of the magnetic mechanism 34 from the magnetically non-attracted position to the magnetically attracted position, so as to provide the magnetically attractive force to the centrifuge tubes 32 containing the target cells 92. As shown in FIG. 12, the target cells 92 move together with the beads 91 to a side of the centrifuge tubes 32 proximate to the magnetic mechanism 34 due to the magnetic attractive force. At this time, solution in the centrifuge tubes 32 can be removed using the pipettor 43 with the target cells 92 conjugated with the beads 91 being attracted to and staying at the side of the centrifuge tube 32. Subsequently, an enzyme solution for breaking the conjugation between the target cells 92 and the beads 91 is added to the centrifuge tubes 32 using the pipettor 43, and then the magnetic mechanism 34 is moved back to the magnetically non-attracted position before a repeated pipetting action is performed for mixing and breaking the conjugation between the target cells 92 and the beads 91. Afterwards, the magnetic mechanism 34 is moved to the magnetically attracted position again to magnetically attract the beads 91 to the side of the centrifuge tubes 32, and solution containing the target cells 92 in each centrifuge tube 32 can be transferred to a centrifuge tube 32 using the pipettor 43, which is then centrifuged. After centrifugation, the supernatant in the centrifuge tube 32 is removed, and the target cells 92 with a relatively high purity are obtained.

The above-mentioned operation is an exemplified operation using the automatic cell isolation and collection system of this disclosure to demonstrate operations of the crush module 2, the centrifuge module 3, the transport module 4, the consumable module 5, and the control unit 8, and operation of the automatic cell isolation and collection system is not limited thereto. In addition to the control unit 8 automatically controlling the operation of each of the crush module 2, the centrifuge module 3, and the transport module 4 (i.e., controlling the entire isolation and collection process from start to finish), the operating interface 7 can be operated for setting the operating parameters, environment parameters (e.g., temperature in the housing 6), and even setting the sequence of detailed operations in each of the steps 901, 902, 903, so as to facilitate implementation of a fully automated and precisely-operated cell isolation and collection process in accordance with the requirements of a user.

In summary, virtue of the control unit 8 controlling the operations of the crush module 2, the centrifuge module 3, and the transport module 4, the entire cell isolation and collection process is automated and can be carried out in a closed environment in the housing 6, thereby eliminating human operator error, effectively reducing operating time, and avoiding sample contamination due to human operation.

In the description above, for the purposes of explanation, numerous specific details have been set forth in order to provide a thorough understanding of the embodiment. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects.

While the disclosure has been described in connection with what is considered the exemplary embodiment, it is understood that this disclosure is not limited to the disclosed embodiment but is intended to cover various arrangements included within the spirit and scope of the broadest interpretation so as to encompass all such modifications and equivalent arrangements.

What is claimed is:

1. An automatic cell isolation and collection system adapted for sorting out target cells from a sample, said automatic cell isolation and collection system comprising:
   a crush module including a container that defines an accommodating space adapted for receiving the sample therein, and a crusher that is removably disposed in said accommodating space and that is for crushing the sample, wherein the crusher includes a rotor, a drive shaft driven rotatably by the rotor, and a blade disposed on the drive shaft and configured to crush the sample when the drive shaft is rotated;
   a centrifuge module spaced apart from said crush module, and including a centrifuge seat, a plurality of spaced-apart centrifuge tubes that are disposed on said centrifuge seat, and a magnetic mechanism that is spaced apart from said centrifuge seat, and that provides a magnetically attractive force to at least one of said centrifuge tubes;
   a transport module disposed along a path between said crush module and said centrifuge module, and including a movable connecting seat, and a pipettor that is co-movably connected to said connecting seat and that is for transferring of the sample and for transferring of a reagent to said centrifuge tubes; and
   a control unit in electrical communication with said crush module, said centrifuge module, and said transport module, and controlling crushing operation of said crush module, transport of the sample via said transport module after the sample is crushed by said crush module, centrifugation of said centrifuge module, and operation of said magnetic mechanism for providing the magnetically attractive force.

2. The automatic cell isolation and collection system as claimed in claim 1, wherein: said crush module and said centrifuge module are spaced apart from each other in a first direction; and said crush module further includes a movable platform which is operable to move in the first direction and on which said container is disposed.

3. The automatic cell isolation and collection system as claimed in claim 2, wherein said transport module further includes a linear rail which extends in the first direction, and which is located above said crush module and said centrifuge module, said connecting seat being disposed on and slidable along said linear rail.

4. The automatic cell isolation and collection system as claimed in claim 3, wherein said pipettor is co-movable with said connecting seat in the first direction, and is movable relative to said linear rail in a second direction which is transverse to said first direction.

5. The automatic cell isolation and collection system as claimed in claim 4, further comprising a consumable module disposed between said crush module and said centrifuge module, located under said transport module, and including a tip case that is formed with a plurality of tip-receiving holes facing upward, and a plurality of pipette tips that are disposed in said tip-receiving holes and that fit on said pipettor.

6. The automatic cell isolation and collection system as claimed in claim 5, wherein said tip case is further formed with a disposal space spaced apart from said tip-receiving holes and for disposal of said pipette tips.

7. The automatic cell isolation and collection system as claimed in claim 5, further comprising a housing defining a closed space in which said crush module, said transport module, said centrifuge module, and said consumable module are disposed.

8. The automatic cell isolation and collection system as claimed in claim 7, further comprising an operating interface disposed on said housing and electrically communicating with said control unit.

9. The automatic cell isolation and collection system as claimed in claim 1, wherein said centrifuge module further includes a step motor that is connected to said centrifuge seat and that is in electrical communication with said control unit.

10. The automatic cell isolation and collection system as claimed in claim 1, wherein said magnetic mechanism is a permanent magnet, and is operable by said control unit to move between a magnetically attracted position, where said magnetic mechanism is proximate to said at least one of said centrifuge tubes so as to provide the magnetically attractive force to said at least one of said centrifuge tubes, and a magnetically non-attracted position, where said magnetic mechanism is distal from said at least one of said centrifuge tubes.

11. The automatic cell isolation and collection system as claimed in claim 1, wherein said magnetic mechanism is an electromagnet, and is operable by said control unit to generate the magnetically attractive force.

* * * * *